(12) United States Patent
Kusumoto et al.

(10) Patent No.: US 7,214,835 B2
(45) Date of Patent: May 8, 2007

(54) 1,7,8-TRIFLUORONAPHTHALENE-2-NAPHTHOL, AND METHOD FOR PRODUCING LIQUID CRYSTAL COMPOUND USING SAME

(75) Inventors: Tetsuo Kusumoto, Ageo (JP); Yutaka Nagashima, Saitama (JP); Sadao Takehara, Sakura (JP); Takashi Matsumoto, Saitama (JP)

(73) Assignee: Dainippon Ink & Chemicals, Inc., Tokyo (JP)

( * ) Notice: Subject to any disclaimer, the term of this patent is extended or adjusted under 35 U.S.C. 154(b) by 231 days.

(21) Appl. No.: 10/527,674

(22) PCT Filed: Sep. 26, 2003

(86) PCT No.: PCT/JP03/12333

§ 371 (c)(1),
(2), (4) Date: Mar. 11, 2005

(87) PCT Pub. No.: WO2004/029015

PCT Pub. Date: Apr. 8, 2004

(65) Prior Publication Data

US 2006/0163537 A1    Jul. 27, 2006

(30) Foreign Application Priority Data

Sep. 27, 2002   (JP)   ............... 2002-282887

(51) Int. Cl.
*C07C 39/38*    (2006.01)
*C07C 43/247*   (2006.01)
*C07C 25/18*    (2006.01)
*C09K 19/32*    (2006.01)

(52) U.S. Cl. .................. 568/737; 568/634; 570/183

(58) Field of Classification Search ................ 568/634, 568/737; 570/127, 129, 130, 183; 252/299.62
See application file for complete search history.

(56) References Cited

FOREIGN PATENT DOCUMENTS

| DE | 195 22 195 A1 | 12/1995 |
|---|---|---|
| JP | 2-4725 | 1/1990 |
| JP | 2-176625 | 7/1990 |
| JP | 5-505247 | 8/1993 |
| JP | 2001-31597 | 2/2001 |
| JP | 2001-40354 | 2/2001 |
| JP | 2004-204133 | * 7/2004 |
| JP | 2004-352931 | * 12/2004 |
| JP | 2005-048007 | * 2/2005 |

OTHER PUBLICATIONS

English translation by computer for JP 2004-352931, http://www4.ipdl.ncipi.go.jp/Tokujitu/PAJdetail.ipdl?N0000=60&N0120=01&N2001=2&N3001=2004-352931.*

English translation by computer for JP 2005-48007, http://www4.ipdl.ncipi.go.jp/Tokujitu/PAJdetail.ipdl?N0000=60&N0120=01&N2001=2&N3001=2005-048007.*

English translation by computer for JP 2004-204133, http://www4.ipdl.ncipi.go.jp/Tokujitu/PAJdetail.ipdl?N0000=60&N0120=01&N2001=2&N3001=2004-204133.*

* cited by examiner

*Primary Examiner*—Shean C Wu
(74) *Attorney, Agent, or Firm*—Armstrong, Kratz, Quintos, Hanson & Brooks, LLP

(57) ABSTRACT

The present invention provides 1,7,8-trifluoro-2-naphthol and a derivative thereof as intermediates for efficiently producing a trifluoronaphthalene liquid crystal material. A method for efficiently producing a trifluoronaphthalene liquid crystal material using such intermediates is also disclosed. A naphthol derivative having the following general formula (I) is disclosed. A method for producing a trifluoronaphthalene compound having the following general formula (IV), (VI) or (VIII) using the naphthol derivative as a raw material is also disclosed

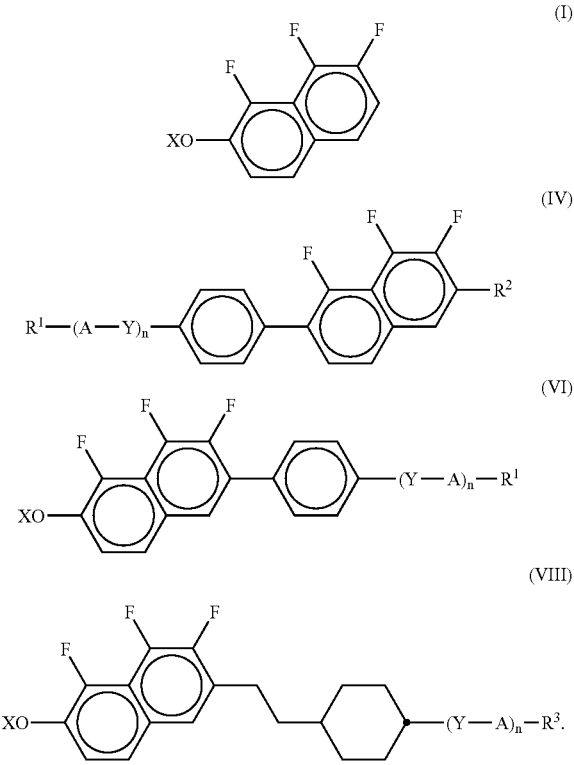

8 Claims, No Drawings

1,7,8-TRIFLUORONAPHTHALENE-2-NAPHTHOL, AND METHOD FOR PRODUCING LIQUID CRYSTAL COMPOUND USING SAME

TECHNICAL FIELD

The present invention relates to a method for producing trifluoronaphthalene compounds useful as a liquid crystal display material and an intermediate thereof.

BACKGROUND ART

TN and STN systems having a twisted structure have mainly been used in liquid crystal display elements. Many liquid crystal compounds and compositions with positive dielectric constant anisotropy, which have significant roles in these TN and STN systems, have been developed. On the other hand, for the purpose of improving the narrowness of view angle which is one of the drawbacks of the above display systems having twisted structure, the display systems such as (1) the system of vertically aligning liquid crystal molecules (VA system; Vertical Alignment system) (for example, there is Japanese Unexamined Patent Application, First Publication No. Hei 2-176625) or (2) the system of rotating liquid crystal molecules in plane horizontal to a substrate by applying voltage (IPS system; In-Plane Switching system) (for example, there is published Japanese translation No. Hei 5-505247 of PCT International Publication) are proposed. In these display systems, the liquid crystal compounds and compositions with negative dielectric anisotropy have a significant role, instead of the liquid crystal compounds and compositions with positive dielectric constant anisotropy which are referred to as indispensable compounds for the display systems having twisted structure. For example, the proposal of the liquid crystal compounds and compositions with negative dielectric constant anisotropy was made in Japanese Unexamined Patent Application, First Publication No. Hei 2-4725.

For the above purpose, the development of the liquid crystal compounds having a 1,7,8-trifluoronaphthalene-2,6-diyl group has been performed. For example, several compounds are disclosed in Japanese Unexamined Patent Application, First Publication No. 2001-31597 and German Patent Application, Publication No. 19522195.

However, the methods for producing these compounds were not necessarily efficient. In Japanese Unexamined Patent Application, First Publication No. 2001-31597, a trifluoronaphthalene derivative described below is produced as an intermediate,

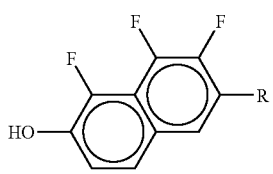

wherein R represents alkyl groups.

On the other hand, in the design of a composition for a liquid crystal composition, a low-volume multiproduct is obligatory since several compounds called homologues, wherein backbones of liquid crystal compounds are the same and side chains are different, are used so as to avoid the deposition of the compounds. For an efficient production, it is preferable to increase the amount to be produced once. To this end, it is of advantage to produce the compound of a common backbone and to introduce different parts at the final stage of the production. In the case of producing two sorts of homologue described below, wherein only R is different, with the method using the intermediate,

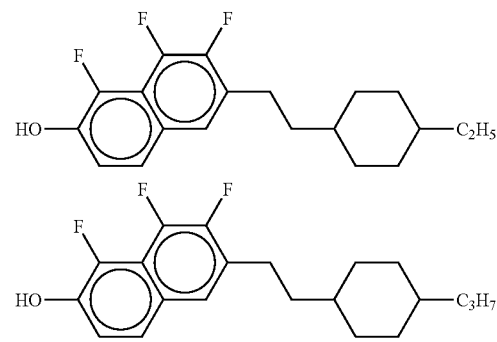

the efficiency was deteriorated since the trifluoronaphthalene backbone should be reproduced from the beginning and many intermediates are necessary. In addition, since the production, whose yield is relatively low, is performed at the final stage of the production, the loss of the high-cost intermediate is large, thereby deteriorating the efficiency badly.

On the other hand, in German Patent Application, Publication No. 19522195, the trifluoronaphthalene derivative is produced by the following pathway,

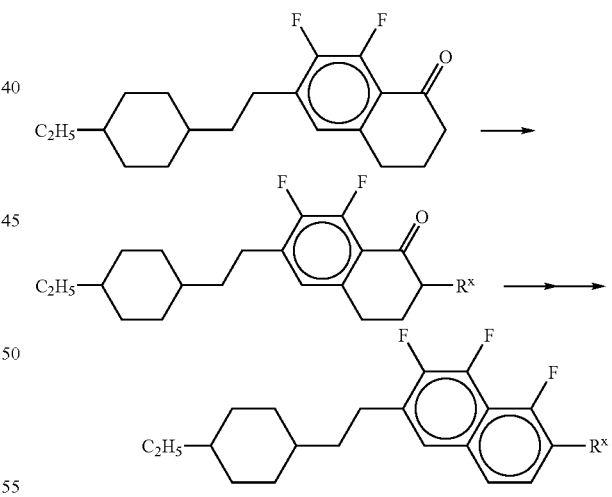

wherein $R^x$ represents alkyl groups.

In this method, it is necessary to prepare many intermediates for the production of the above homologue. Furthermore, since $R^x$ cannot connect the naphthalene backbone through an oxygen atom, the liquid crystal compounds, which the invention of the present application aims at, cannot be produced.

Therefore, it is desired to develop the trifluoronaphthalene derivatives, wherein it is possible to previously form the trifluoronaphthalene backbone and to introduce the other backbone later, and an efficient method for producing trifluoronaphthalene using these intermediates.

DISCLOSURE OF INVENTION

Objects of the present invention are to provide 1,7,8-trifluoronaphthalene-2-naphthol and derivatives thereof as intermediates for efficiently producing a trifluoronaphthalene liquid crystal material and to provide a method for efficiently producing trifluoronaphthalene liquid crystal material using the same.

The present inventors have intensively researched the solution of the above objects. Then, they have developed the method using 1,7,8-trifluoronaphthalene-2-naphthol and derivatives thereof as intermediates, and thus the present invention has been completed.

The present invention provides a compound represented by general formula (I),

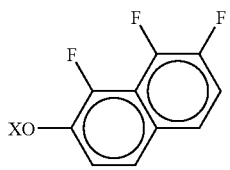
(I)

wherein X represents a hydrogen atom, $CF_3SO_2$—, or a saturated or unsaturated alkyl group having a carbon number of 1 to 10.

Also, the present invention provides a method for producing a compound represented by general formula (III) by reacting a compound represented by general formula (Ia) with a compound represented by general formula (II) in the presence of a catalyst,

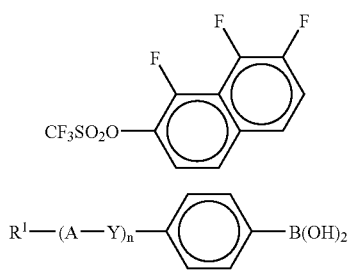
(Ia)
(II)

wherein $R^1$ represents a saturated or unsaturated alkyl group having a carbon number of 1 to 10, and Y represents a single bond, —$CH_2CH_2$—, or —$CH_2O$—, and A represents a trans-1,4-cyclohexylene group or a 1,4-phenylene group, and n represents a number of 0 or 1,

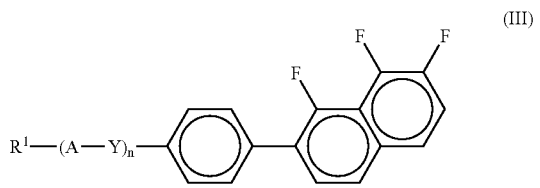
(III)

wherein $R^1$, Y, A, and n represent the same as in general formula (II).

Moreover, the present invention provides a method for producing a compound represented by general formula (IV) comprising reacting a compound represented by general formula (Ia) with a compound represented by general formula (II) in the presence of a catalyst to produce a compound represented by general formula (III) and alkylating or alkoxylating the compound represented by general formula (III),

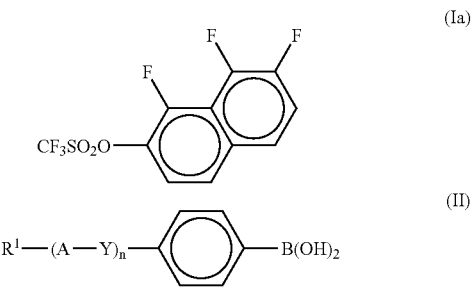
(Ia)
(II)

wherein $R^1$ represents a saturated or unsaturated alkyl group having a carbon number of 1 to 10, and Y represents a single bond, —$CH_2CH_2$—, or —$CH_2O$—, and A represents a trans-1,4-cyclohexylene group or a 1,4-phenylene group, and n represents a number of 0 or 1,

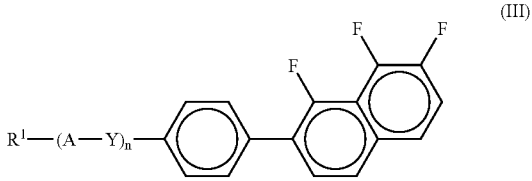
(III)

wherein $R^1$, Y, A, and n represent the same as in general formula (II),

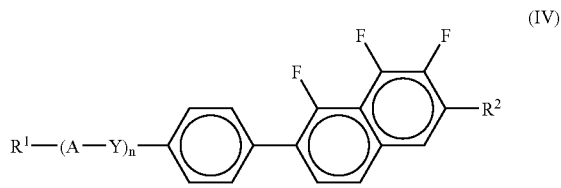
(IV)

wherein $R^1$, Y, A, and n represent the same as in the general formula (II), and $R^2$ represents a saturated or unsaturated alkyl or alkoxyl group having a carbon number of 1 to 10.

Furthermore, the present invention provides a method for producing a compound represented by general formula (VI) comprising lithiating the 6-position of a compound represented by general formula (Ib), reacting the compound represented by general formula (Ib) with trimethoxyborane to produce boronic acid, and reacting the boronic acid with a compound represented by general formula (V) in the presence of a catalyst,

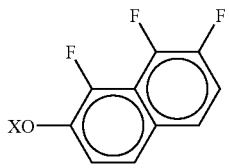

wherein X represents a saturated or unsaturated alkyl group having a carbon number of 1 to 10,

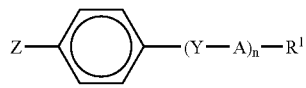

wherein Z represents an iodine atom, a bromine atom, a chlorine atom, or a trifluoromethanesulfonyloxy group, and R¹ represents a saturated or unsaturated alkyl group having a carbon number of 1 to 10, and Y represents a single bond, —CH₂CH₂—, or —CH₂O—, A represents a trans-1,4-cyclohexylene group or a 1,4-phenylene group, and n represents a number of 0 or 1,

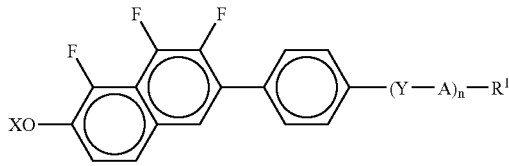

wherein X and R¹ represent saturated or unsaturated alkyl groups having a carbon number of 1 to 10, and Y represents a single bond, —CH₂CH₂—, or —CH₂O—, and A represents a trans-1,4-cyclohexylene group or a 1,4-phenylene group, and n represents a number of 0 or 1.

In addition, the present invention provides a method for producing a compound represented by general formula (VIII) comprising lithiating the 6-position of a compound represented by general formula (Ib), reacting the compound represented by general formula (Ib) with a cyclohexylacetoaldehyde derivative represented by general formula (VII), dehydrating a product obtained by the reaction between the compounds represented by general formulae (Ib) and (VII), and hydrogenating a double bond produced by the dehydration,

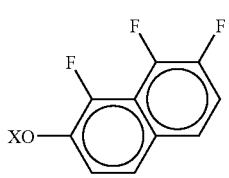

wherein X represents a saturated or unsaturated alkyl group having a carbon number of 1 to 10,

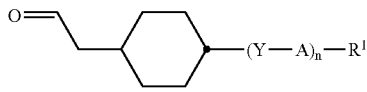

wherein R¹ represents a saturated or unsaturated alkyl group having a carbon number of 1 to 10, and Y represents a single bond, —CH₂CH₂—, or —CH₂O—, and A represents a trans-1,4-cyclohexylene group or a 1,4-phenylene group, and n represents a number of 0 or 1,

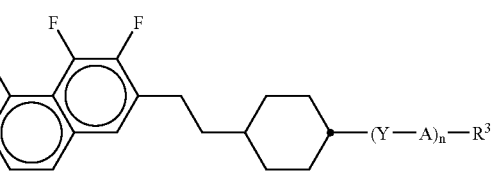

wherein X and R³ represent saturated alkyl groups having a carbon number of 1 to 10, and Y represents a single bond, —CH₂CH₂—, or —CH₂O—, and A represents trans-1,4-cyclohexylene group or 1,4-phenylene group, and n represents a number of 0 or 1.

The compound represented by general formula (I), wherein X═H, can be obtained by fluorinating 7,8-difluoro-2-naphthol; moreover, by reacting this compound with a trifluoromethanesulfonyl anhydrate, the compound represented by general formula (I), wherein X═CF₃SO₂—, can be obtained. Also, the compound represented by general formula (I), wherein X represents a saturated or unsaturated alkyl group having a carbon number of 1 to 10, can be obtained by reacting with a corresponding alkyl halide in the presence of the base such as potassium carbonate, sodium carbonate, or sodium hydride.

In the fluorination, fluoropyridiniums such as N-fluoropyridinium triflate, N-fluoropyridinium tetrafluoroborate, N-fluoro-2,6-dichloropyridinium triflate, N-fluoro-2,6-dichloropyridinium tetrafluoroborate, N-fluro-2,4,6-trimethylpyridinium triflate, N-fluoro-2,4,6-trimetylpyridinium tetrafluoroborate, N,N'-difluoro-2,2'-bipyridinium bis(tetrafluoroborate), or N-fluoro-4,6-dimethylpyridinium-2-sulfonate; fluoroammoniums such as 1-chloromethyl-4-fluoro-1,4-diazoniabicyclo[2.2.2]octanebis (tetrafluoroborate); or electron-withdrawing fluorinating agents such as a fluorine gas, bromine trifluoride, or iodine pentafluoride can be used. While, in the fluorination, 1,1,7,8-tetrafluoro-1,2-dihydronaphthalene-2-one can be produced besides the desired 1,7,8-trifluoro-2-naphthol, it can be easily transformed into 1,7,8-trifluoro-2-naphthol by reducing it with a reducing agent such as a hydrogen.

Here, 7,8-difluoro-2-naphthol, which is a starting material in the fluorination, can be produced by making the acid chloride from 2,3-difluorophenylacetic acid and reacting the 7,8-difluoro-1,2,3,4-tetrahydronaphthalene, which is produced by reacting the acid chloride with ethylene in the presence of aluminium chloride, with an oxidizing agent such as a bromine as described below.

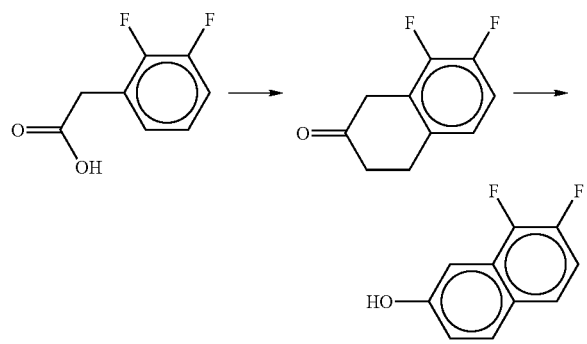

Also, in the compound represented by general formula (I), wherein X represents a saturated or unsaturated alkyl group having a carbon number of 1 to 10, examples of X include a saturated alkyl group such as a methyl group, an ethyl group, a propyl group, a butyl group, a pentyl group, a hexyl group, a heptyl group, an octyl group, a nonyl group, a decyl group, or a 2-methylbutyl group; and an unsaturated alkyl group such as an aryl group or a crotyl group. Here, examples of an alkyl halide used for the synthesis include methyl iodide, ethyl iodide, propyl iodide, butyl iodide, pentyl iodide, hexyl iodide, heptyl iodide, octyl iodide, nonyl iodide, decyl iodide, 2-methylbutyl iodide, methyl bromide, ethyl bromide, propyl bromide, butyl bromide, pentyl bromide, hexyl bromide, heptyl bromide, octyl bromide, nonyl bromide, decyl bromide, 2-methylbutyl bromide, methyl chloride, ethyl chloride, propyl chloride, butyl chloride, pentyl chloride, hexyl chloride, heptyl chloride, octyl chloride, nonyl chloride, decyl chloride, 2-methylbutyl chloride, allyl bromide, crotyl bromide, allyl chloride, and crotyl chloride.

In the production of the compound represented by general formula (IV), the reaction between the triflate of general formula (I) (X=CF$_3$SO$_2$—) and the boronic acid of general formula (II) to produce the compound represented by general formula (III) is called the Suzuki coupling.

In this reaction, a mixture system (binary system) of water and an organic solvent can be used as a reaction solvent. As an organic solvent, single or mixture of nitrils such as acetonitrile or benzonitrile; halogen type solvents such as dichloromethane, chloroform, carbon tetrachloride, 1,2-dichloroethane, or 1,1,1-trichloroethane; ethers such as diethyl ether, methyl-t-butyl ether, or tetrahydrofuran; esters such as ethyl acetate, methyl acetate, or butyl acetate; saturated hydrocarbons such as pentane, hexane, heptane, or octane; benzenes such as benzene, toluene, xylene, or chlorobenzene; or amides such as N,N-dimethylformaldehyde or N,N-dimethylacetoamide can be used, while tetrahydrofuran, toluene, or xylene is preferable.

The reaction can be performed at a temperature which is not less than the boiling point of either an organic solvent or water or the azeotropic point thereof under the normal pressure. For example, in the water-THF(tetrahydrofuran) binary system, 80 to 200° C. is preferable, and 90 to 130° C. is particularly preferable.

As the base used in the reaction, inorganic bases such as sodium carbonate, potassium carbonate, sodium hydroxide, potassium hydroxide, sodium hydrogencarbonate, potassium hydrogencarbonate, magnesium carbonate, or calcium carbonate can be used, while sodium carbonate, potassium carbonate, sodium hydroxide, or potassium hydroxide is preferable, and sodium carbonate or potassium carbonate is particularly preferable.

Examples of the catalyst used in the reaction include a palladium complex such as tetrakis(triphenylphosphine)palladium, dichlorobis(triphenylphosphine)palladium, dichlorobis[(diphenylphosphino)ethane]palladium, dichlorobis[(diphenylphosphino)propane]palladium, dichlorobis[(diphenylphosphino)butane]palladium, or dichlorobis[(diphenylphosphino)ferrocene]palladium; and a nickel complex such as tetrakis(triphenylphosphine)nickel, dichlorobis(triphenylphosphine)nickel, dichlorobis[(diphenylphosphino)ethane]nickel, dichlorobis[(diphenylphosphino)propane]nickel, dichlorobis[(diphenylphosphino)butane]nickel, or dichlorobis[(diphenylphosphino)ferrocene]nickel, while a palladium complex is preferable.

Moreover, the method of refluxing with heating using a palladium catalyst and the binary system solvent between water and tetrahydrofuran, benzene, toluene, or xylene in the presence of sodium carbonate or potassium carbonate is particularly preferable in this reaction.

In the production of the phenylnaphthalene compound described as the general formula (IV) (in the case in which $R^2$ is an alkyl group) by the alkylation of the general formula (III), the alkylation can be performed as follows.

The 6-position of the naphthalene ring of general formula (III) is selectively lithiated and then reacted with an alkyl iodide or an allyl halide to produce the phenylnaphthalene compound represented by general formula (IV).

In this reaction, it is preferable for the lithiation to use alkyllithium such as butyllithium, s-butyllithium, or t-butyllithium; or lithium amide such as lithium diisopropoxide or lithium hexamethyldisilazide.

It is preferable to perform this reaction in an organic solvent. A nonaqueous polar solvent such as tetrahydrofuran, diethyl ether, or dimethoxyethane; or a hydrocarbon type solvent such as benzene, toluene, xylene, hexane, or heptane is preferable.

Specific examples of alkyl iodide include methyl iodide, ethyl iodide, propyl iodide, and butyl iodide. Specific examples of allyl iodide include allyl chloride, allyl bromide, crotyl chloride, and crotyl bromide.

In the production of the phenylnaphthalene compound represented by general formula (IV) (in the case in which $R^2$ is an alkyl group) by the alkoxylation of general formula (III), the alkoxylation can be performed as follows.

The 6-position of the naphthalene ring of general formula (III) is selectively lithiated and then reacted with trimethoxyborane followed by a hydrogen peroxide to produce the naphthol at the 6-position of which a hydroxyl group is introduced. Then, the naphthol is reacted with alkyl halide or allyl halide to produce the phenylnaphthalene compound represented by general formula (IV).

In these reactions, it is preferable for the lithiation to use alkyllithium such as butyllithium, s-butyllithium, or t-butyllithium; or lithium amide such as lithium diisopropoxide or lithium hexamethyldisilazide.

It is preferable to perform these reactions in an organic solvent. A nonaqueous polar solvent such as tetrahydrofuran, diethyl ether, or dimethoxyethane; or a hydrocarbon type solvent such as benzene, toluene, xylene, hexane, or heptane is preferable.

Specific examples of alkyl iodide include methyl iodide, ethyl iodide, propyl iodide, and butyl iodide. Specific examples of allyl iodide include allyl chloride, allyl bromide, crotyl chloride, and crotyl bromide.

The boronic acid represented by general formula (II) is often used as the intermediate for the production of a liquid crystal. For example, the boronic acid can be easily produced by reacting the Grignard reagent, which is produced by reacting the phenyl bromide represented by general formula (Va) with a magnesium, with trimethoxyborane,

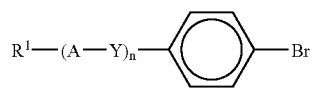

(Va)

wherein $R^1$, Y, A, and n represent the same as in general formula (II).

The compound described as general formula (VI) can be produced by the Suzuki coupling which reacts boronic acid, which is easily produced by selectively lithiating and reacting with trimethoxyboran the 6-position of the compound represented by general formula (I) (X represents a saturated or unsaturated alkyl group having a carbon number of 1 to 10), with the compound represented by general formula (V).

The reaction conditions in the above production of the compound represented by general formula (IV) can be directly used in the Suzuki coupling.

It is preferable for the selective lithiation at the 6-position of the compound described as the general formula (I) (X represents saturated or unsaturated alkyl groups having a carbon number of 1 to 10) to use alkyllithium such as butyllithium, s-butyllithium, or t-butyllithium or lithium amide such as lithium diisopropoxide or lithium hexamethyldisilazide.

It is preferable for the lithiation to use single or mixture of a nonaqueous polar solvent such as tetrahydrofuran, diethyl ether, or dimethoxyethane or a hydrocarbon type solvent such as benzene, toluene, xylene, hexane, or heptane.

The temperature of the lithiation is within a range of 0° C. to the solidifying point, while a range of −20 to −90° C. is preferable, and a range of −40 to −78° C. is particularly preferable.

Also, the compound represented by general formula (V) is often used as the intermediate for the production of a liquid crystal, and the procurement of this compound is easy.

Examples of the method for producing the compound represented by general formula (VIII) include the method, wherein the 6-position of the compound represented by general formula (I), wherein X represents a saturated or unsaturated alkyl group having a carbon number of 1 to 10, is lithiated selectively and reacted with the cyclohexylacetoaldehyde derivative represented by general formula (VII) to produce the alcohol represented by general formula (IX), and this alcohol is dehydrated to produce the compound represented by general formula (X), and the olefin portion of it is hydrogenated,

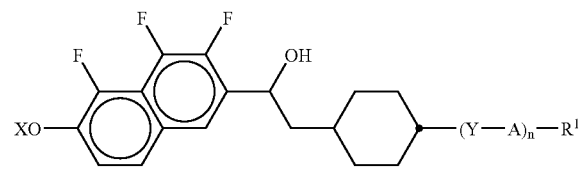

(IX)

wherein X and $R^1$ represent saturated or unsaturated alkyl group having a carbon number of 1 to 10, and Y represents a single bond, —CH$_2$CH$_2$—, or —CH$_2$O—, and A represents trans-1,4-cyclohexylene group or 1,4-phenylene group, and n represents a number of 0 or 1,

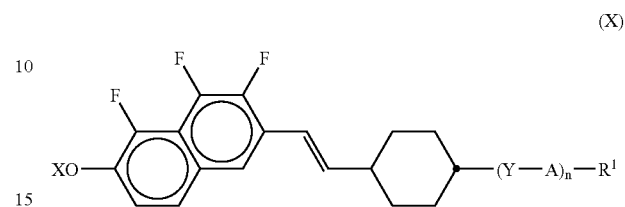

(X)

wherein X, $R^1$, Y, A, and n represent the same as in general formula (IX).

The conditions in the selective lithiation at the 6-position of the compound represented by general formula (I) is same as it in the method for producing the compound represented by general formula (VI).

In the reaction between the lithiated compound represented by general formula (I) and the cyclohexylacetoaldehyde derivative represented by general formula (VII), the aldehyde may be dissolved in the same solvent as used for the lithiation and then added in the reaction solution after the lithiation.

The reaction temperature in the reaction is within a range of room temperature to the solidifying temperature, while a range of 0 to −60° C. is preferable.

For the dehydration, there is no problem in the generally well-known conditions. Examples of dehydration include the method of refluxing with heating in toluene in the presence of an acid-catalyst such as sulfuric acid or p-toluenesulfonic acid or the method of reacting with methyl chloride and tosyl chloride in the presence of the base such as pyridine.

Also, the hydrogenation of an olefin is well-known and easily performed by using the catalyst such as palladium-carbon or Raney nickel in a hydrogen atmosphere or under increased pressure.

EXAMPLES

The following examples further illustrate the present invention in detail, while the present invention is not limited to these examples.

Example 1

The production of 1,7,8-trifluoro-2-naphthol (general formula (I): X=a hydrogen atom).

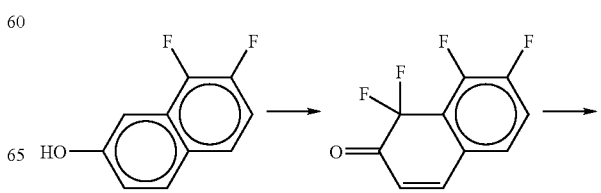

-continued

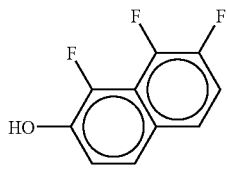

N,N'-difluoro-2,2'-bipiridinium bis(tetrafluoroborate) (53 g) was added to an acetonitrile (240 ml) solution of 7,8-difluoro-2-naphthol (26 g), and the reaction solution was refluxed with heating for 3.5 hours. The reaction solution was poured into water. The organic layer was removed, and the aqueous layer was extracted 3 times with ethyl acetate. The organic layers were combined, washed 2 times with a saturated saline solution, and concentrated. The crude product of 1,1,7,8-tetrafluoro-1,2-dihydronaphthalen-2-one is obtained as a residue. The residue, 5% of palladium-carbon (possessing 50% water, 5 g), silica gel (5 g), and ethyl acetate (200 ml) were added in an autoclave and stirred for 4 hours at room temperature under pressurized hydrogen (4 kg/cm$^2$). The reaction solution was filtrated, and the filtrate was concentrated. The residue was recrystallized from the mixed solvent of hexane/toluene, and 1,7,8-trifluoro-2-naphthol was obtained as light yellow crystals.

Melting point: 91° C. $^1$H NMR (CDCl$_3$) δ 5.0–6.5 (broad, 1 H), 7.14–7.24 (m, 2 H), 7.45–7.55 (m, 2 H) MS m/z: 198 (M$^+$, 100)

Example 2

The production of 1,7,8-trifluoronaphthalene-2-yl trifluoromethanesulfonate (general formula (I): X=CF$_3$SO$_2$—).

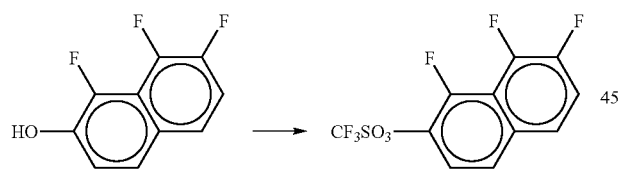

Pyridine (10 ml) was added slowly and dropwise to a dichloromethane (60 ml) solution of 1,7,8-trifluoro-2-naphthol (10 g) and trifluoromethanesulfonic acid anhydrate (10.3 ml) at the temperature of the ice/water, and then the reaction solution was stirred for 30 minutes. Water and dichloromethane were added slowly in the reaction solution. The organic layer was removed, and the aqueous layer was extracted with dichloromethane. The organic layers were combined, washed with water, 10% hydrochloric acid, a saturated sodium hydroxide aqueous solution, water, and brine consecutively, and concentrated. The residue was purified by column chromatography (silica gel, hexane/ethyl acetate=19/1), and 1,7,8-trifluoronaphthalene-2-yl trifluoromethanesulfonate was obtained as light yellow crystals.

MS m/z: 330 (M$^+$), 169 (100)

Example 3

The production of 2-ethoxy-1,7,8-trifluoronaphthalene (general formula (I): X=ethyl group).

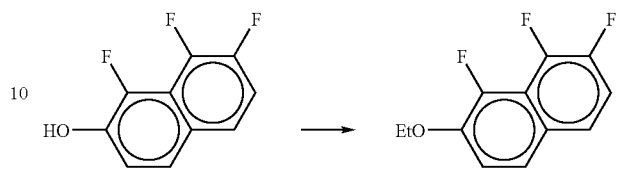

An acetone (80 ml) solution of 1,7,8-trifluoro-2-naphthol (15 g), potassium carbonate (16 g), and ethyl iodide (26 g) was stirred for 10 hours at room temperature. Toluene (200 ml) was added in this reaction solution. The organic layer was removed, and the aqueous layer was extracted with toluene. The organic layers were combined, washed with brine, and concentrated. The residue was evaporated under reduced pressure, and 2-ethoxy-1,7,8-trifluoronaphthalene was obtained.

Melting point: 96.5 to 98.5° C. $^1$H NMR (CDCl$_3$) δ 1.48 (t, J=7.1 Hz, 3 H), 4.27 (q, J=7.1 Hz, 2H), 7.15–7.35 (m, 2 H), 7.45–7.60 (m, 2 H) MS m/z: 226 (M$^+$), 198 (100)

Example 4

The production of 2-(4-propylphenyl)-1,7,8-trifluoronaphthalene (general formula (III): R$^1$=propyl group, n=0).

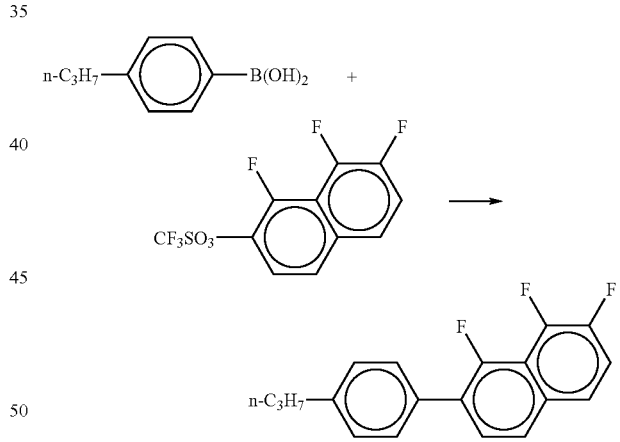

1,7,8-Trifluoronaphthalene-2-yl trifluoromethanesulfonate (15 g), 4-propylphenylboric acid (11.2 g), potassium carbonate (18.8 g), tetrakis(triphenylphosphine)palladium(0) (1 g), toluene (50 ml), tetrahydrofuran (50 ml), and water (20 ml) were added in an autoclave and stirred for 4 hours at 90° C. under pressurized nitrogen (2 kg/cm$^2$). The reaction solution was poured into water. The organic layer was removed, and the aqueous layer was extracted with toluene. The organic layers were combined, washed with 10% hydrochloric acid and brine, and concentrated. The residue was purified by column chromatography (silica gel, hexane), and 2-(4-propylphenyl)-1,7,8-trifluoronaphthalene was obtained.

MS m/z: 300 (M$^+$), 271 (100)

Example 5

The production of 3-methyl-7-(4-propylphenyl)-1,2,8-trifluoronaphthalene (general formula (IV): $R^1$=propyl group, n=0, $R^2$=methyl group).

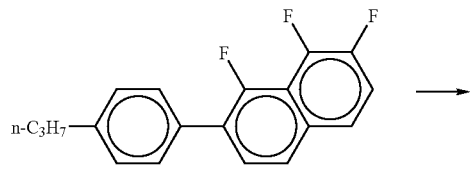

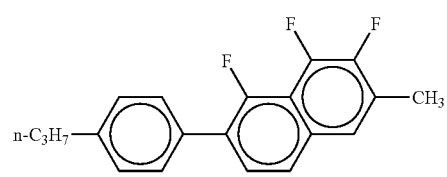

A 1.58 M butyllithium/hexane solution (16.4 ml) was added dropwise to a tetrahydrofuran (25 ml) solution of 2-(4-propylphenyl)-1,7,8-trifluoronaphthalene (6.5 g) at −65° C., and the reaction solution was stirred for 1 hour. A tetrahydrofuran (25 ml) solution of methyl iodide (3.7 g) was added dropwise to this reaction solution for 30 minutes, and then the reaction temperature was increased to room temperature. Water was added to the reaction solution. After stirring, a small amount of a hydrochloric acid was added to neutralize the reaction solution. The organic layer was removed, and the aqueous layer was extracted with ethyl acetate. The organic layers were combined, washed with water, a sodium thiosulfate aqueous solution, and brine, and concentrated. The residue was purified by column chromatography (silica gel, hexane) and recrystallized from ethanol (2 times), and 2-(4-propylphenyl)-1,7,8-trifluoronaphthalene was obtained as colorless needles.

Melting point: 99° C. $^1$H NMR (CDCl$_3$) δ 0.99 (t, J=7.3 Hz, 3 H), 1.70 (sextet, J=7.3 Hz, 2 H), 2.49 (s, 3 H), 2.66 (t, J=7.3 Hz, 2 H), 7.2–7.6 (m, 7 H) MS m/z: 314 (M$^+$), 285 (100)

Comparative Example 1

The production of 3-methyl-7-(4-propylphenyl)-1,2,8-trifluoronaphthalene.

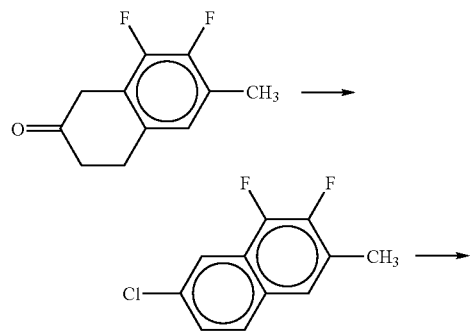

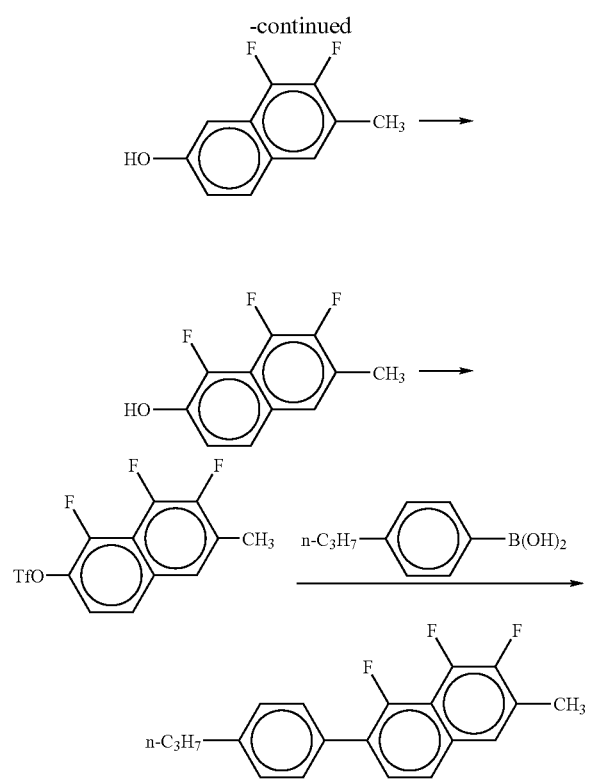

The production of 3-methyl-7-(4-propylphenyl)-1,2,8-trifluoronaphthalene was performed with the method described in Japanese Unexamined Patent Application, First Publication No. Hei 6-157954 (pages 2 3 5 6) using 7,8-difluoro-1,2,3,4-tetrahydronaphthalen-2-one as a starting material. In this method, the yield of 2-chloro-6-methyl-7,8-difluoronaphthalene is reduced, and the number of steps is many; therefore, the efficient production could not be performed. Also, since the intermediates with different side chains needed to be prepared in the case of producing the compounds with different side chains, the efficiency was deteriorated.

Example 6

The production of 3-ethoxy-7-(4-propylphenyl)-1,2,8-trifluoronaphthalene (general formula (IV): $R^1$=propyl group, n=0, $R^2$=ethoxy group).

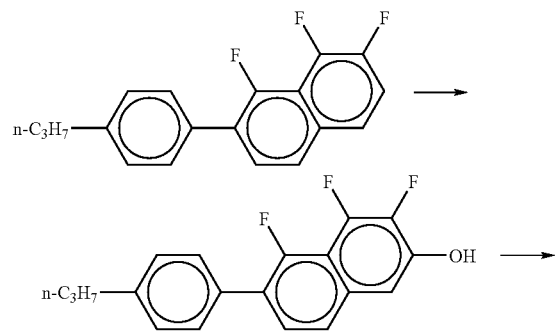

-continued

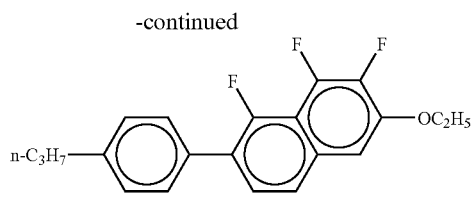

A 1.58 M butyllithium/hexane solution (16.4 ml) was added dropwise to a tetrahydrofuran (25 ml) solution of 2-(4-propylphenyl)-1,7,8-trifluoronaphthalene (6.5 g) at −65° C., and the reaction solution was stirred for 1 hour. A tetrahydrofuran (25 ml) solution of methyl iodide (3.7 g) was added dropwise to the reaction solution for 30 minutes, and then the reaction temperature was increased to 0° C. Acetic acid (1.85 ml) and 30% hydrogen peroxide (3 ml) were added to the reaction solution, followed by stirring for a while. Water was added to the reaction solution. The organic layer was removed, and the aqueous layer was extracted with ethyl acetate. The organic layers were combined, washed with water and brine, and concentrated. Then, 6-(4-propylphenyl)-3,4,5-trifluoro-2-naphthol was obtained.

MS m/z: 316 (M$^+$), 287 (100)

A N,N-dimethylformamide (30 ml) solution of 6-(4-propylphenyl)-3,4,5-trifluoro-2-naphthol was added dropwise to a N,N-dimethylformamide (5 ml) suspension of sodium hydride (60% oiliness, 1.3 g) while cooled with ice. A N,N-dimethylformamide (20 ml) solution of ethyl iodide (6.3 g) was added dropwise to the reaction solution for 30 minutes, followed by stirring for another 30 minutes.

The reaction solution was poured into water, and sodium thiosulfate was added to it. After stirring for a while, the organic layer was removed, and the aqueous layer was extracted with ethyl acetate. The organic layers were combined, washed with brine, and concentrated. The residue was purified by column chromatography (silica gel, toluene), and recrystallized from ethanol (3 times). Then, 3-ethoxy-7-(4-propylphenyl)-1,2,8-trifluoronaphthalene (3.8 g) was obtained.

Melting point: 122° C. $^1$H NMR (CDCl$_3$) δ 0.99 (t, J=7.3 Hz, 3 H), 1.55 (t, J=7.1 Hz, 3 H), 1.72 (broad sextet, J=7.6Hz, 2 H), 2.65 (t, J=7.6Hz, 2 H), 4.23 (q, J=7.1 Hz, 2 H), 7.0–7.6 (m, 7 H)

MS m/z: 344 (M$^+$), 287 (100)

Example 7

The production of 7-ethoxy-3-[4-(trans-4-propylcyclohexyl)phenyl]-1,2,8-trifluoronaphthalene (general formula (VI): R$^1$=propyl group, A=cyclohexyl group, Y=single bond, n=1, X=ethyl group).

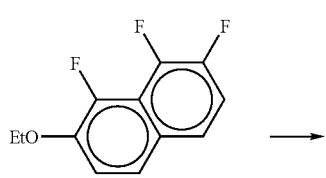

-continued

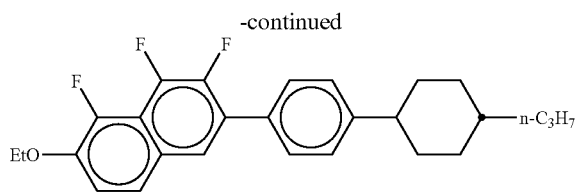

A tetrahydrofuran (80 ml) solution of 2-ethoxy-1,7,8-trifluoronaphthalene (16 g) was cooled to −60° C. Then, a 1.58 M butyllithium/hexane solution (16.4 ml) was added dropwise to this solution, followed by stirring for 1 hour. Trimethoxyborane (8.8 g) was added for 30 minutes, and then the reaction temperature was increased to room temperature. The reaction solution was poured into 10% hydrochloric acid. The organic layer was removed, and the aqueous layer was extracted with toluene. The organic layers were combined, washed with 10% hydrochloric acid and brine, and concentrated. The residue was purified by column chromatography (alumina, toluene/hexane=1/3) and recrystallized from toluene/hexane. Then, 7-ethoxy-3-[4-(trans-4-propylcyclohexyl)phenyl]-1,2,8-trifluoronaphthalene (6 g) was obtained.

Phase transition temperatures: Cr 134 N 248 I $^1$H NMR (CDCl$_3$) δ 0.92 (t, J=7.1 Hz, 3 H), 1.00–1.15 (m, 2 H), 1.45 (m, 5 H), 1.45–1.60 (m, 5 H), 1.92 (t, J=16.4Hz, 4 H), 2.54 (t, J=12.5 Hz, 1 H), 4.28 (q, J=6.8 Hz, 2H), 7.20–7.35 (m, 3 H), 7.50–7.60 (m, 4 H) MS m/z: 426 (M$^-$, 100)

Example 8

The production of 7-ethoxy-3-[2-[trans-4-(trans-4-butylcyclohexyl)cyclohexyl]phenyl]-1,2,8-trifluoronaphthalene (general formula (VIII): R$^3$=butyl group, A=cyclohexyl group, Y=single bond, n=1, R$^1$=ethyl group).

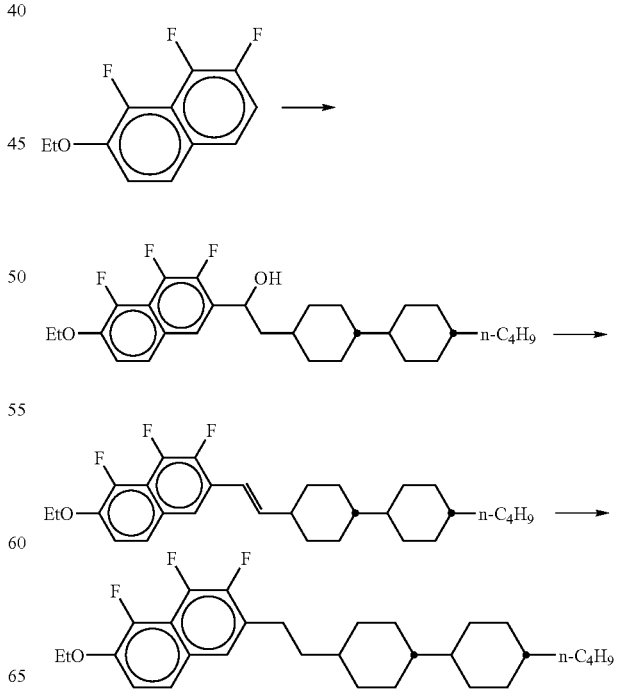

A tetrahydrofuran (50 ml) solution of 2-ethoxy-1,7,8-trifluoronaphthalene (9.4 g) was cooled to −60° C. Then, a 1.58 M butyllithium/hexane solution (47 ml) was added dropwise to this solution, followed by stirring for 2 hours. A tetrahydrofuran (50 ml) solution of trans-4-(trans-4-butylcyclohexyl)cyclohexylacetoaldehyde (13.2 g) was added dropwise at −50° C. . After stirring for 2 hours, the reaction temperature was increased to 0° C. 10% hydrochloric acid was added to the reaction solution. The reaction solution was extracted with ethyl acetate, washed with brine, and concentrated. The residue was recrystallized from ethyl acetate, and 7-ethoxy-3-[2-[trans-4-(trans-4-butylcyclohexyl)cyclohexyl]-1-hydroxyethyl]-1,2,8-trifluoronaphthalene was obtained.

A toluene (100 ml) solution of 7-ethoxy-3-[2-[trans-4-(trans-4-butylcyclohexyl)cyclohexyl]-1-hydroxyethyl]-1,2,8-trifluoronaphthalene and p-toluenesulfonic acid (0.6 g) was refluxed with heating in an autoclave for 1 hour. The reaction solution was washed with water and brine, and concentrated. The crude production of (E)-7-ethoxy-3-[2-[trans-4-(trans-4-butylcyclohexyl)cyclohexyl]ethenyl]-1,2,8-trifluoronaphthalene (16.6 g) was obtained.

The crude production of (E)-7-ethoxy-3-[2-[trans-4-(trans-4-butylcyclohexyl)cyclohexyl]ethenyl]-1,2,8-trifluoronaphthalene (16.6 g), 5% palladium-carbon (with 10% moisture) (3.1 g), tetrahydrofuran (100 ml) were added in an autoclave and reacted for 4 hours at room temperature under 4 atm of hydrogen. The reaction solution was filtrated with celite, and the filtrate was concentrated. Then, 7-ethoxy-3-[2-[trans-4-(trans-4-butylcyclohexyl)cyclohexyl]phenyl]-1,2,8-trifluoronaphthalene (9 g) was obtained.

Phase transition temperatures: Cr 94 N 209 I $^1$H NMR (CDCl$_3$) δ 0.82–0.89 (m, 5 H), 0.94–1.01 (m, 8 H), 1.12–1.27 (m, 8 H), 1.46 (t, J=7.0 Hz, 3 H), 1.52–1.57 (m, 2 H), 1.67–1.75 (m, 6 H), 1.83–1.85 (m, 2 H), 2.74–2.78 (m, 2 H), 4.24 (q, J=7.0 Hz, 2 H), 7.20 (dd, J=9.0 and 6.6 Hz, 1 H), 7.29–7.30 (broad d, J=8 Hz, 1 H), 7.24–7.44 (broad dt, J=9.0 and 1.0 Hz, 1 H) MS m/z: 474 (M$^+$, 100)

INDUSTRIAL APPLICABILITY

A 1,7,8-trifluoronaphthalene-2-naphthol derivative and a method for efficiently producing trifluoronaphthalene liquid crystal material using the same provided by the present invention enable to produce a liquid crystal compound having a trifluoronaphthalene backbone which has been difficult to produce in the past.

The invention claimed is:

1. A compound represented by general formula (I),

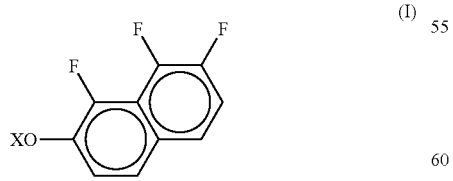

(I)

wherein X represents a hydrogen atom, CF$_3$SO$_2$—, or a saturated or unsaturated alkyl group having a carbon number of 1 to 10.

2. A compound according to claim 1, wherein X represents a hydrogen atom.

3. A compound according to claim 1, wherein X represents CF$_3$SO$_2$—.

4. A compound according to claim 1, wherein X represents a saturated or unsaturated alkyl group having a carbon number of 1 to 10.

5. A method for producing a compound represented by general formula (III) by reacting a compound represented by general formula (Ia) with a compound represented by general formula (II) in the presence of a catalyst,

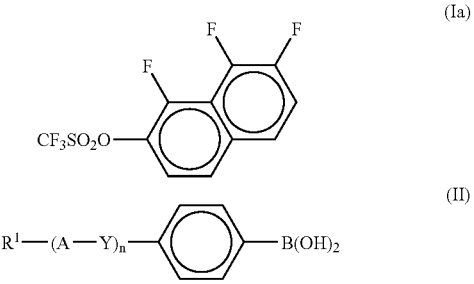

(Ia)

(II)

wherein R$^1$ represents a saturated or unsaturated alkyl group having a carbon number of 1 to 10, and Y represents a single bond, —CH$_2$CH$_2$—, or —CH$_2$O—, and A represents a trans-1,4-cyclohexylene group or a 1,4-phenylene group, and n represents a number of 0 or 1,

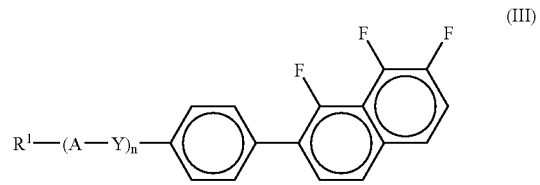

(III)

wherein R$^1$, Y, A, and n represent the same as in general formula (II).

6. A method for producing a compound represented by general formula (IV) comprising:

reacting a compound represented by general formula (Ia) with a compound represented by general formula (II) in the presence of a catalyst to produce a compound represented by general formula (III); and alkylating or alkoxylating the compound represented by general formula (III),

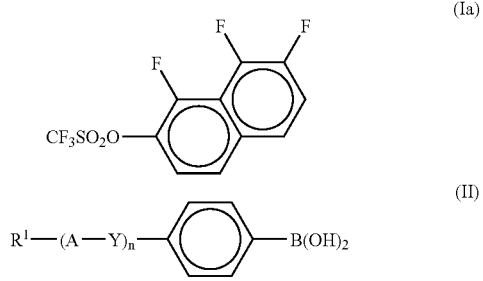

(Ia)

(II)

wherein R$^1$ represents a saturated or unsaturated alkyl group having a carbon number of 1 to 10, and Y represents a single bond, —CH$_2$CH$_2$—, or —CH$_2$O—, and A represents a trans-1,4-cyclohexylene group or a 1,4-phenylene group, and n represents a number of 0 or 1,

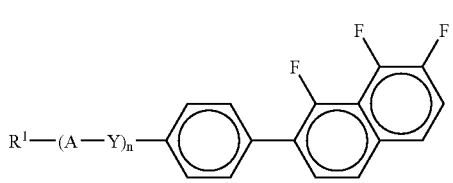

(III)

wherein R¹, Y, A, and n represent the same as in general formula (II),

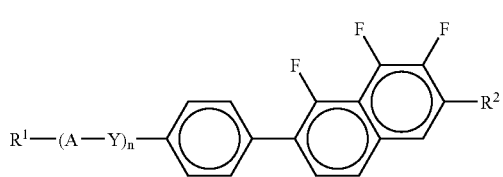

(IV)

wherein R¹, Y, A, and n represent the same as in the general formula (II), and R² represents a saturated or unsaturated alkyl or alkoxyl group having a carbon number of 1 to 10.

7. A method for producing a compound represented by general formula (VI) comprising:

lithiating 6-position of a compound represented by general formula (Ib);

reacting the compound represented by general formula (Ib) with trimethoxyborane to produce boronic acid; and reacting the boronic acid with a compound represented by general formula (V) in the presence of a catalyst,

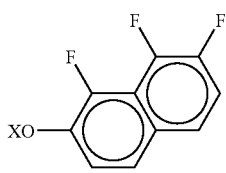

(Ib)

wherein X represents a saturated or unsaturated alkyl group having a carbon number of 1 to 10,

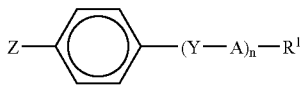

(V)

wherein Z represents an iodine atom, a bromine atom, a chlorine atom, or a trifluoromethanesulfonyloxy group, and R¹ represents a saturated or unsaturated alkyl group having a carbon number of 1 to 10, and Y represents a single bond, —CH₂CH₂—, or —CH₂O—, A represents a trans-1,4-cyclohexylene group or a 1,4-phenylene group, and n represents a number of 0 or 1,

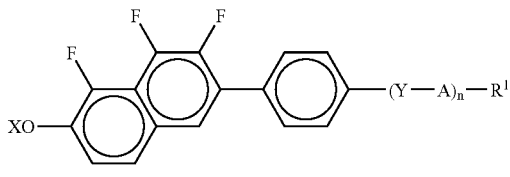

(VI)

wherein X and R¹ represent saturated or unsaturated alkyl groups having a carbon number of 1 to 10, and Y represents a single bond, —CH₂CH₂—, or —CH₂O—, and A represents a trans-1,4-cyclohexylene group or a 1,4-phenylene group, and n represents a number of 0 or 1.

8. A method for producing a compound represented by general formula (VIII) comprising:

lithiating 6-position of a compound represented by general formula (Ib);

reacting the compound represented by general formula (Ib) with a cyclohexylacetoaldehyde derivative represented by general formula (VII);

dehydrating a product obtained by the reaction between the compounds represented by general formulae (Ib) and (VII); and hydrogenating a double bond produced by the dehydration,

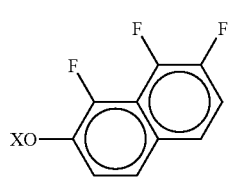

(Ib)

wherein X represents a saturated or unsaturated alkyl group having a carbon number of 1 to 10,

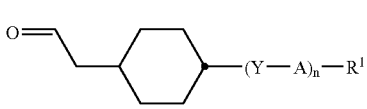

(VII)

wherein R¹ represents a saturated or unsaturated alkyl group having a carbon number of 1 to 10, and Y represents a single bond, —CH₂CH₂—, or —CH₂O—, and A represents a trans-1,4-cyclohexylene group or a 1,4-phenylene group, and n represents a number of 0 or 1,

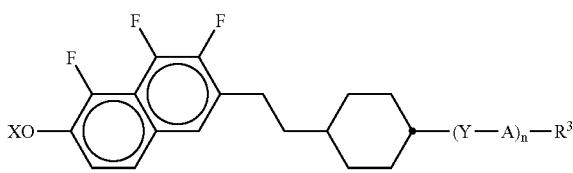

(VIII)

wherein X and R³ represent saturated alkyl groups having a carbon number of 1 to 10, and Y represents a single bond, —CH₂CH₂—, or —CH₂O—, and A represents trans-1,4-cyclohexylene group or 1,4-phenylene group, and n represents a number of 0 or 1.

* * * * *